United States Patent [19]

Deckert

[11] Patent Number: 4,533,347
[45] Date of Patent: Aug. 6, 1985

[54] CONTROLLER FOR A DUAL DRUG DELIVERY SYSTEM

[75] Inventor: Clinton L. Deckert, Poway, Calif.

[73] Assignee: Warner-Lambert Company, Morris Plains, N.J.

[21] Appl. No.: 562,958

[22] Filed: Dec. 19, 1983

[51] Int. Cl.³ ............................................. A61M 5/00
[52] U.S. Cl. ..................................... 604/81; 604/250
[58] Field of Search ............... 604/82, 80, 81, 83–86, 604/157, 151–153, 246, 250, 251, 65

[56] References Cited

U.S. PATENT DOCUMENTS

| | | | |
|---|---|---|---|
| 3,886,937 | 6/1975 | Bobo et al. | 128/214 |
| 4,034,754 | 7/1977 | Virag | 128/214 |
| 4,038,981 | 8/1977 | Le Fevre | 604/65 |
| 4,094,318 | 6/1978 | Burke et al. | 128/214 |
| 4,105,029 | 8/1978 | Virag | 128/214 |
| 4,219,022 | 8/1980 | Genese | 128/214 |
| 4,236,515 | 12/1980 | Genese | 128/214 |
| 4,237,880 | 12/1980 | Genese | 128/214 |
| 4,250,879 | 2/1981 | Muetterties | 128/214 |
| 4,256,103 | 3/1981 | Mylrea | 128/214 |
| 4,256,105 | 3/1981 | Leahey et al. | 128/214 |
| 4,258,712 | 3/1981 | Harms et al. | 128/214 |
| 4,265,240 | 5/1981 | Jenkins | 128/214 |
| 4,300,552 | 11/1981 | Cannon | 604/65 |
| 4,324,238 | 4/1982 | Genese et al. | 128/214 |
| 4,391,598 | 7/1983 | Thompson | 604/65 |
| 4,451,255 | 5/1984 | Bujan et al. | 604/81 X |

FOREIGN PATENT DOCUMENTS 2059776  4/1981  United Kingdom .

*Primary Examiner*—Stephen C. Pellegrino

*Attorney, Agent, or Firm*—Neil K. Nydegger

[57] ABSTRACT

A system for controlling the flow of intravenous fluids to a patient provides for the sequential administration of two different intravenous fluids at independently preselected drop rates. The system includes a primary administration set associated with a first fluid container, a secondary administration set associated with a second fluid container, and a controller having a control valve operatively associated with both administration sets to control the fluid flow rate through the particular administration set in use. The system further comprises a connector means in the primary administration set, upstream from the control valve, for joining the secondary administration set to the primary administration set. A one-way valve, disposed in the primary administration set upstream from the connector means, prevents fluid flow through the one-way valve whenever hydrostatic pressure in the secondary set is greater than the hydrostatic pressure in the primary set. Drop sensors, operatively associated with drip chambers in each of the administration sets, are electrically connected with the controller to monitor and sense whether there is fluid flow in the particular system. The controller also includes a pinching device which is activated to pinch IV tubing in the secondary set when the controller either senses no flow rate through the secondary set or senses a sufficient flow rate in the primary set. This pinching action causes an instantaneous reversal of the hydrostatic pressure differential at the one-way valve and permits immediate fluid flow from the first fluid container at a controlled rate through the primary administration set to the patient.

6 Claims, 4 Drawing Figures

CONTROLLER FOR A DUAL DRUG DELIVERY SYSTEM

BACKGROUND OF THE INVENTION

The present invention relates to systems and equipment sets for the administration of liquids. More particularly, the present invention relates to a system which sequentially administers medical solutions at preselected rates with a single controller. The present invention is particularly, but not exclusively, useful in the health care field for the intravenous administration of medical solutions to patients.

DESCRIPTION OF THE PRIOR ART

Intravenous drug delivery systems have been used in the health care field for many years. These systems typically include a solution container and associated tubing for delivery of medical solutions from the container to the patient. In the past the equipment used in such systems has ranged from the standard system which includes only the container and the associated tubing to the more sophisticated systems wherein a controller or a pump is associated with the tubing set to assist in the administration of the fluid. An example of a pump used for the above stated purpose is set forth in U.S. Pat. No. 3,985,133 which is assigned to the assignee of the present invention. An example of a controller used in an IV system is set forth in U.S. Pat. No. 4,300,552 also assigned to the same assignee as the present invention.

Although the standard sets have typically provided for the administration of a single fluid, the need to administer two different fluids to a patient is not uncommon. Typically, such a need arises when a patient must have a maintenance solution delivered and, concomitantly with the administration of the maintenance fluid, there is a need for the infusion of a therapeutic solution. In such cases it has been the practice to use what is commonly referred to as a "piggyback" system wherein separate fluids from separate containers are sequentially infused through a common tube. Such systems have several obvious advantages. For instance, in a piggyback system the needle need not be removed from the patient whenever the administration of fluids changes from the maintenance solution to the therapeutic solution or vice versa. This fact, of course, causes less trauma to the patient, avoids unnecessary pain, and reduces the chances of infection. Furthermore, and equally important, the use of a piggyback system simplifies procedures for the nurse.

Several devices have been proposed for the sequential administration of two separate solutions to a patient. Basically, these systems comprise a primary administration set and a secondary administration set and rely on the differential of hydrostatic pressure between these sets at a check valve for the sequencing of fluid flow within the system. Often also incorporated into piggyback systems is a float valve or an air impermeable membrane in the secondary system which prevents air from getting into the primary system after fluid flow has stopped in the secondary system.

Several examples of basic piggyback systems can be found in the prior art. For instance, U.S. Pat. No. 3,886,937 to Bobo et al. and U.S. Pat. No. 4,034,754 to Virag disclose IV administration sets that follow the basic principles for a piggyback system. Further, it has been proposed that flow rates through the secondary set and the primary set be controlled so that different flow rates can be achieved. Often, this has been achieved by incorporating clamping devices with each of the administration sets. Examples of such clamping arrangements are set forth in U.S. Pat. No. 4,250,879 to Muetterties and in U.S. Pat. No. 4,219,022 to Genese. Also, in a variation on this theme, it has been proposed that flow rates within the primary system of a piggyback configuration be established by restrictive inner diameters in the tubing such as is disclosed in U.S. Pat. No. 4,105,029 to Virag and in U.S. Pat. No. 4,256,105 to Leahey et al.

It has also been proposed that a controller, instead of clamps or restrictions, be used in a piggyback system for controlling the flow rates. U.S. Pat. No. 4,094,318 to Burke et al. and U.S. Pat. No. 4,265,240 to Jenkins and assigned to the assignee of the present invention disclose systems wherein a controller is used to control flow rates. In these devices, however, two control means are required and a separate control means must be inserted into each of the fluid paths for independent control of flow rate through the respective paths. U.S. Pat. No. 4,391,598 to Thompson discloses a piggyback system comprising a single controller in combination with a passive metering unit. In this system, infusion is accomplished by the timed activation of an alternating clamping mechanism associated with the fluid lines.

There is, however, still a need for a single simplified controller in a piggyback IV system which alternately controls the flow rate in both the primary system and in the secondary system. More specifically, there is a need for a controller which uses a direct measurement of the rate of fluid flow through each system and compares the sensed actual rate with a preselected desired rate for controlling the actual flow rate. Additionally, there is a need for a controller which permits prolonged use of the tubing associated with the system and does not require its replacement each time the fluid containers themselves are to be changed.

Accordingly, it is an object of the present invention to provide a cost effective and easily operated system for the sequential administration of separate medical solutions. It is another object of the present invention to provide a controller which allows the operator to preselect separate drop rates for administration of medical solutions from a primary set and from a secondary set. It is yet another object of the present invention to provide a controller and a system which allows the operator to preselect a drop rate for the secondary administration set and to place the secondary set into operative connection with the primary set for subsequent introduction of fluid from the secondary set. It is yet another object of the present invention to provide a piggyback system which automatically switches to the primary administration set upon completion of infusion of fluid from the secondary fluid container. Still another object of the invention is to provide a means for leaving fluid in the secondary administration set upon completion of infusion of fluid from the secondary fluid container so that only the fluid container itself needs to be changed.

SUMMARY OF THE INVENTION

The preferred embodiment of the sequential controller for a dual IV solution delivery system comprises a primary administration set having a drip chamber and a one-way valve disposed in its associated tubing. The device further comprises a secondary administration set which has a drip chamber and a pinchable section disposed in its associated tubing. A connector means provides for fluid communication from each of the administration sets into a common tube. A controller is operatively associated with the common tube for controlling the rate of fluid flow through the common tube. Further, the controller has means connected with the respective drip chamber of the primary and secondary administration sets for monitoring and sensing the drop rate through the drip chamber. The controller also includes means to compare the actual drop rate with a preselected drop rate programmed into the controller. By comparing the actual drop rate with the respective preselected drop rate, the controller adjusts the control means associated with the common tubing to control the rate of flow through the common tube The one-way valve in the primary administration set prevents back flow into the primary administration set during fluid flow through the secondary administration set. A further function of the controller is to provide a pinching device which is operatively associated with the pinching section of the secondary set to prevent fluid flow through the secondary set whenever there is no fluid remaining in the secondary fluid container or after fluid flow has begun in the primary administration set.

The novel features of this invention as well as the invention itself both as to its organization and operation will be best understood from the accompanying drawings taken in conjunction with the accompanying description in which similar reference characteristics refer to similar parts and in which:

BRIEF DESCRIPTION OF THE DRAWINGS

FIG. 4 is a cross-sectional view of the pinch clamp mechanism used in the controller of the present invention.

DESCRIPTION OF THE PREFERRED EMBODIMENT

Figure 1:
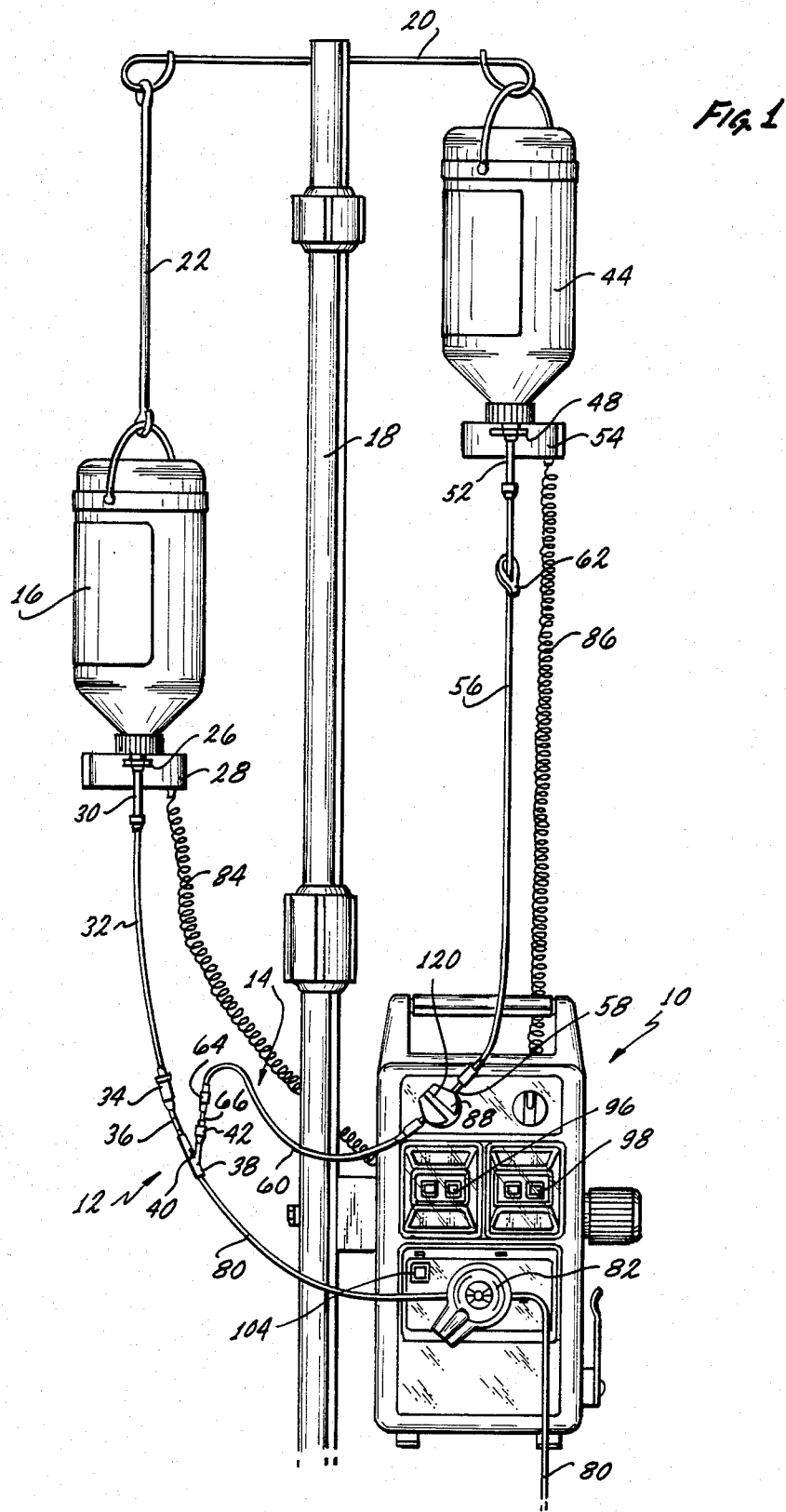
FIG. 1 is a front elevational view of the present invention.

Referring initially to FIG. 1, a set up of the present invention is shown in combination with a controller generally designated 10. As shown in FIG. 1, controller 10 is capable of controlling the fluid flow from two separate fluid sources at preselected flow rates.

Figure 2:
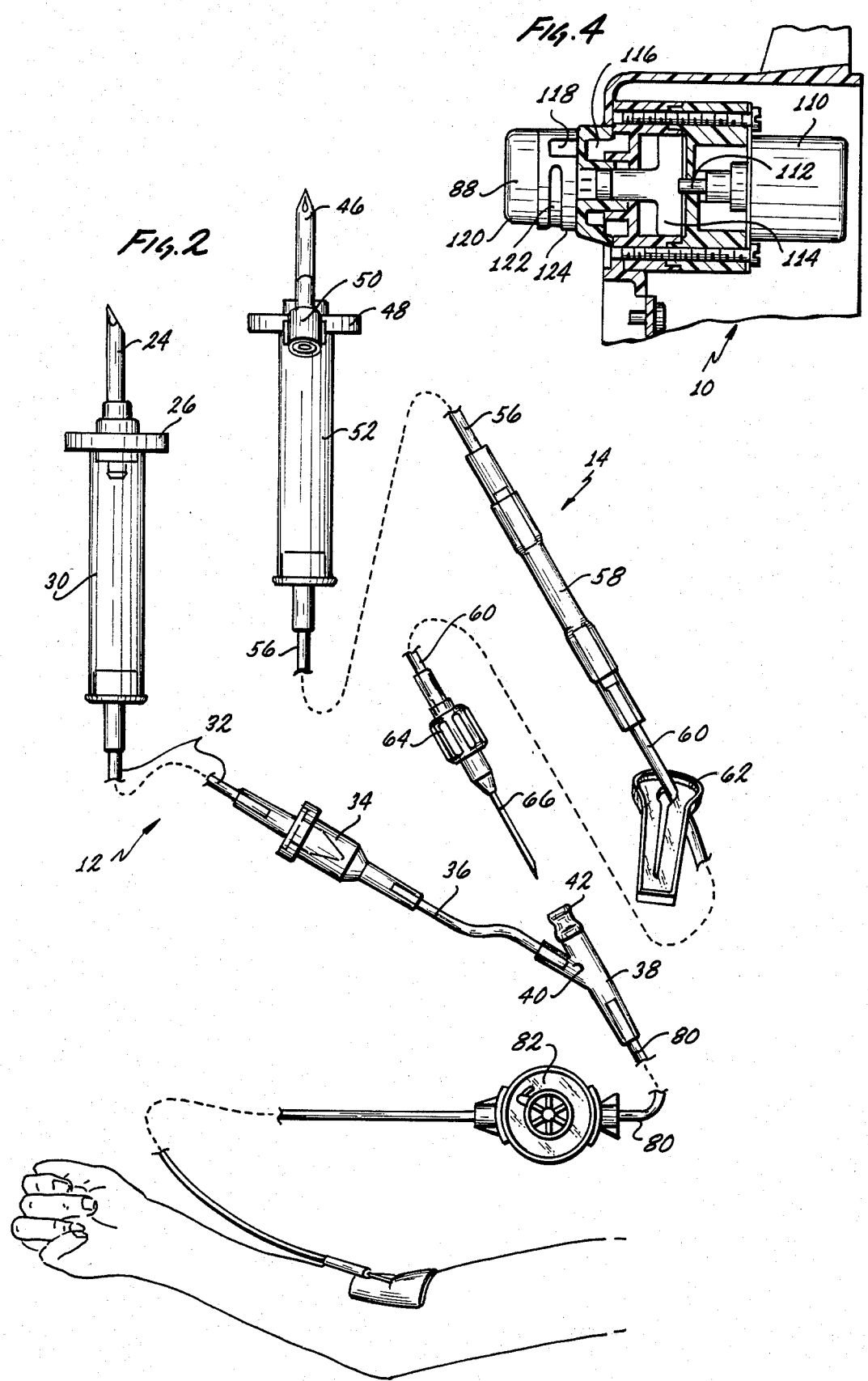
FIG. 2 is a view of the tubing and associated connectors of the present invention with portions disconnected and broken away for clarification.

Referring now to FIG. 2, it is seen that the preferred embodiment comprises a primary administration set generally designated 12 and a secondary administration set generally designated 14. As shown primary administration set 12 includes a standard drip chamber 30, of a construction well known in the art. Associated with the drip chamber 30 is a mounting flange 26 and a spike 24 which is adapted to connect drip chamber 30 in fluid communication with a first fluid container 16. Also attached to the drip chamber 30 by any means well known in the art, such as by solvent bonding, is a tubing section 32. Attached at the end of tubing section 32 opposite from drip chamber 30, by any means well known in the art, such as solvent bonding, is a check valve 34 that is preferably of the duck bill valve type. Associated downstream from check valve 34 and attached thereto by any means well known in the art is a tubing section 36. Tubing section 36 is attached opposite check valve 34 to branch 40 of the connector 38. Connector 38 is a device well known in the art that is commonly referred to as a Y-site connection. As illustrated in FIG. 2, associated with the connector 38 is a rubber stoppel 42 which is penetrable by a needle or other sharp instrument.

Still referring to FIG. 2, it is seen that secondary administration set 14 includes a standard drip chamber 52 having a mounting flange 48 and an attached spike 46 by which drip chamber 52 can be engaged for fluid communication with a second fluid container 44. In FIG. 2 a vent 50 associated with mounting flange 48 is shown with drip chamber 52. Drip chamber 52 may, however, be without a vent 50 and be the same as drip chamber 30. Also, drip chamber 30 of primary administration set 12 may incorporate a vent (not shown) and thus be of the same configuration as drip chamber 52. As shown in FIG. 2, a tubing section 56 is connected for fluid communication between drip chamber 52 and a pinchable section 58. Pinchable section 58 is preferably made of a silicone rubber, but it should be recognized that any resilient material would be suitable for this purpose. As is shown in FIG. 2, pinchable section 58 is attached to the tubing 56 by any suitable means and is attached by the same means to a tubing section 60. The end of tubing section 60 opposite from pinchable section 58 is attached to a link 64 which has a needle 66 associated therewith that is adapted for penetration into stoppel 42 of connector 38 to obtain fluid communication between the secondary administration set 14 and fluid connector 38. It should also be recognized that this connection between needle 66 and stoppel 42 places both the secondary administration set 14 and the primary administration set 12 into fluid communication with connector 38.

Attached to connector 38 by any means well known in the art is a section of common tube 80. As is seen in FIG. 2, common tube 80 is operatively associated with flow rate control valve 82 and, as will be subsequently discussed, flow rate control valve 82 is in turn operatively associated with the controller 10 for controlling the flow rate of fluid from either the primary administration set 12 or the secondary administration set 14.

Referring back to FIG. 1, it is seen that a drop sensor 28 is operatively connected to the drip chamber 30 by engagement of the mounting flange 26 of drip chamber 30 into recesses (not shown) formed on the drop sensor 28. Although there are many possible configurations for drop sensor 28, a drop sensor as disclosed in U.S. Pat. No. 4,346,606 to Cannon et al. and assigned to the assignee of record of this application is suitable. Accordingly, the disclosure and teachings of U.S. Pat. No. 4,346,606 are incorporated herein by reference. As can also be seen in FIG. 1, the drop sensor 28 is electrically connected to the controller 10 by cable 84.

Secondary administration set 14 has incorporated therewith a drop sensor 54 which is operatively connected to drip chamber 52 by engagement of mounting flange 48 into recesses (not shown) formed on the drop sensor 54. As with the drop sensor 28, the drop sensor 54 can be of any suitable type well known in the art. However, in the preferred embodiment it has been found that a drop sensor as disclosed in U.S. Pat. No. 4,346,606 is suitable. Connection of the drop sensor 54 with the controller 10 is accomplished by electrical connection through cable 86. Also as can be seen in both FIG. 1 and FIG. 2, secondary administration set 14 has associated with it a sliding clamp 62 which can be used by the operator to prevent fluid flow through the secondary administration set 14 as desired.

When the entire system of the present invention is assembled, it is seen that the fluid passageway to the patient from either fluid container 16 or fluid container 44 is completed by common tube 80 in association with the flow rate control valve 82. For the purposes of the present invention, a flow rate control valve of the type disclosed in U.S. Pat. No. 4,300,552 to Cannon and assigned to the assignee of record of the present application is preferred. Accordingly, the disclosure and teachings of U.S. Pat. No. 4,300,552 are incorporated herein by reference.

Pinch clamp 88 as shown in FIG. 4 and FIG. 1 is mounted on controller 10 and is operatively associated with a pinch motor 110. A rod 112 is driven by pinch motor 110 and in accordance with the operation of pinch motor 110 moves a constrictor 114. The connection between rod 112 and constrictor can be by any means well known in the art. In the preferred embodiment, rod 112 and constrictor 114 are screwably connected. The pinch clamp 88 also includes a tube holder 124 mounted on controller 10 which has a channel 118 formed therein. Rotatably mounted on tube holder 124 is latch 120 which is rotated to an open position to allow for placement of pinchable section 58 into the channel 118 of tube holder 124. A magnet (not shown) is mounted in latch 120. Hall effect device 116 is located in relation to pinch clamp 88 so that upon closing of the latch 120, the Hall effect device 116 is effectively in the magnetic field of the magnet (not shown) mounted in latch 120. With this structure, the Hall effect device 116, when energized, generates a signal which is transmitted to the electronic componentry of controller 10 whenever the latch 120 is in the closed position. With latch 120 closed, pinch motor 110 can be operated to move rod 112. Thus, when pinchable section 58 of the secondary administration set 14 is positioned in channel 118 with latch 120 in a closed position, pinchable section 58 is held between constrictor 114 and the anvil 122 of latch 120. Activation of pinch motor 110 moves rod 112 and urges constrictor 114 against the pinchable section 58 of secondary administration set 14 to pinch or constrict pinchable section 58 within the pinch clamp 88 to prevent fluid flow therethrough.

Figure 3:
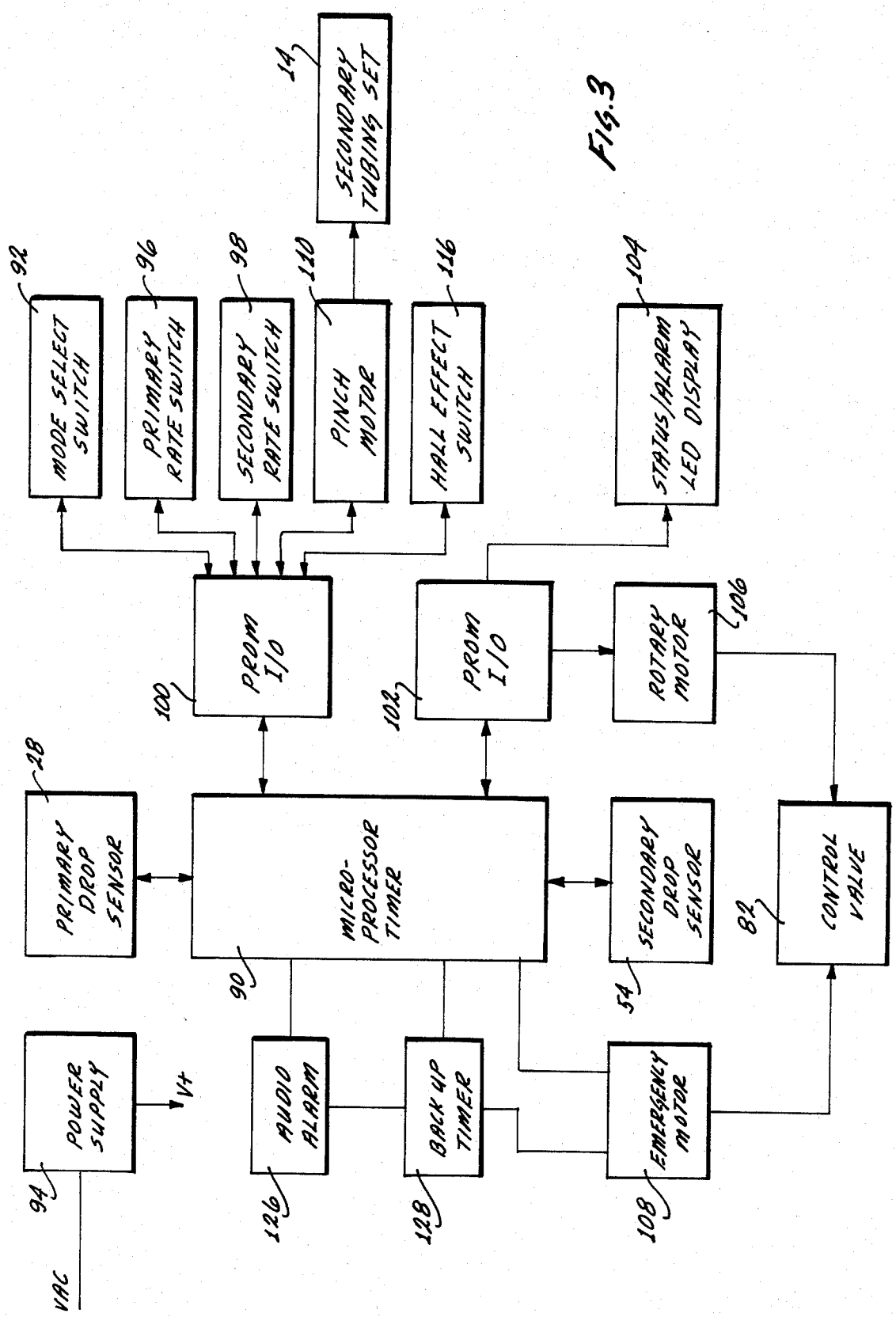
FIG. 3 is a block diagram of the electronic componentry in the controller of the present invention.

A block diagram of the requisite electrical circuits and the associated mechanical devices of controller 10 are presented in FIG. 3. As can be appreciated from the block diagram, a programmed microprocessor 90 is central to the controller 10 and the operation of its electronic components. Power supply 94, which may comprise batteries well known in the art, supplies the voltage necessary to power electronic circuitry and electromechanical devices. Microprocessor 90 may comprise a Model 8039 manufactured by INTEL Corporation having a random access memory (RAM), central processing unit (CPU) and timer. However, any other suitable device may be employed to perform the function of microprocessor 90. It would be obvious to one trained in the pertinent art that the functions of microprocessor 90 may be duplicated by hard wired electronics. Therefore, it should be understood that it is within the scope of the present invention to substitute such an electronic control without departing from the scope and spirit of the invention. Nevertheless, a microprocessor based control device such as Model 8039 is preferred.

A programmable read only memory (PROM) having an Input/Output (I/O) function, designated PROM I/O 100, is electrically connected with microprocessor 90. For purposes of the present invention, a PROM I/O such as Model 8755 manufactured by INTEL Corporation is preferred. This particular model is electrically programmable and erasable. It should be appreciated, however, that any other suitable device capable of performing similar functions may be used as replacement for PROM I/O 100. In addition to PROM I/O 100, a second PROM I/O 102 is also electrically connected with microprocessor 90. Preferably, PROM I/O 102 like PROM I/O 100 is a Model 8755 manufactured by INTEL Corporation. It will be appreciated by one skilled in the pertinent art that the use of both PROM I/O 100 and PROM I/O 102 effectively increases the capacity of controller 10 for programmable memory and number of access ports. Further, it will be appreciated that portions of the system program can be conveniently stored in either PROM I/O 100 or PROM I/0 102 depending on the desires and needs of the programmer. Thus, the system program can run over from PROM I/O 100 to PROM I/O 102.

In the preferred embodiment, PROM I/O 100 interconnects microprocessor 90 to the operator input controls of controller 10. More specifically, PROM I/O 100 provides the input/output function for the primary rate switch 96 and the secondary rate switch 98 and controls their functioning in controller 10. Also electronically connected with PROM I/O 100 is pinch motor 110 and Hall effect device 116. The system program for operating pinch motor 110 for sensing activation of Hall effect device 116 and for application of the preselected drop rates set by the operator on rate switches 96 and 98 are programmed into PROM I/O 100 and are available to microprocessor 90. With specific regard to the preselected drop rates set by the operator on rate switches 96 and 98, it is preferable to have the preselected rates signaled both in BCD form and in BCD compliment. Microprocessor 90 through PROM I/O 100 can then compare both signals to ensure proper operation of the primary rate switch 96 and the secondary rate switch 98. Also, electrical connection between mode select switch 92 and PROM I/O 100 provides the means for energizing the system by power supply 94.

PROM I/O 102 interconnects microprocessor 90 with seven segment L.E.D. display 104 and rotary motor 106. Seven segment L.E.D. 104 is of a type well known in the pertinent art and is electrically connected with microprocessor 90 in a conventional manner to process functional status information pertaining to controller 10 and the IV infusion system. For example, such information as system occlusion, low battery, defective drop sensor, and defective emergency shut off can be assigned a status code and be appropriately shown on display 104 for viewing by the operator. Microprocessor 90 can be programmed by a procedure well known in the art to accomplish proper activation of display 104. Also interconnected with PROM I/O 102 is rotary motor 106 which operatively acts on control valve 82 to control the flow of fluid through common tube 80. The exact manner of interaction between the rotary motor 106 and the control valve 82 is, in all essential functions, similar to the process disclosed in previously cited U.S. Pat. No. 4,300,552. The system program for activating display 104 and operating rotary motor 106 is available to microprocessor 90 with the input/output function provided by PROM I/O 102. Also shown in FIG. 3 is emergency motor 108 which is interconnected between microprocessor 90 and flow rate control valve 82. Upon activation by microprocessor 90, such as would occur when rotary motor 106 becomes inoperative, emergency motor 108 shuts down flow rate control valve 82 to prevent fluid flow through common tube 80. A back up timer 128 is electrically interconnected with microprocessor 90, audio alarm 126 and emergency motor 108 so as to activate emergency motor 108 and audio alarm 126 and shut down flow rate control valve 82 in the event microprocessor 90 fails. Also, audio alarm 126 is interconnected with microprocessor 90, as shown in FIG. 3, to alarm whenever any programmed alarm condition is sensed by microprocessor 90. Back up timer 128 provides another function by providing an input to microprocessor 90 to check the timer (not shown) in microprocessor 90.

OPERATION

In the operation of the present invention, it will be appreciated by reference to FIG. 1 that first fluid container 16 is suspended from the cross bar 20 of an IV pole 18 by an extension hanger 22. Second fluid container 44, on the other hand, is suspended directly from cross bar 20 of IV pole 18. Slide clamp 62 is closed to prevent fluid flow in secondary administration set 14, and spike 46 is connected with second fluid container 4 for fluid communication between container 44 and drip chamber 52. Pinchable section 58 of secondary administration set 14 is then seated into channel 118 of tube holder 124, and latch 120 is closed to retain pinchable section 58 within pinch clamp 88. Slide clamp 62 is then opened to allow fluid flow through secondary administration set 14 for the purpose of purging air from tubing 56 and 60, pinchable section 58 and needle 66. After this purge operation clamp 62 is again closed. Primary administration set 12 is connected in fluid communication with first fluid container 16 by operatively connecting spike 24 with container 16. Fluid from first fluid container 16 is allowed to purge primary administration set 12 by manipulation of control valve 82. Control valve 82 is then closed to prevent flow through primary administration set 12. Secondary administration set 14 is then connected to primary administration set 12 by sticking needle 66 into stoppel 42 of connector 38. Flow rate control valve 82, disposed in the fluid passageway of common tube 80, is then operatively connected with controller 10. At this time, clamp 62 can be opened.

When connected in the above manner, it will be appreciated by one familiar with the art that the hydrostatic pressure in the secondary administration set 14 exceeds the hydrostatic pressure of the primary administration set 12 whenever the fluid level in second fluid container 44 is higher than the fluid level in first fluid container 16. This will remain so while the pinch clamp 88 is in an opened position to allow unrestricted fluid flow through the secondary administration set 14. It will also be appreciated to one skilled in the pertinent art that the hydrostatic pressure differential between the secondary administration set 14 and the primary administration set 12 will manifest itself at check valve 34 by preventing the flow of fluid from the secondary set in a reverse direction through the check valve 34 and into tubing 32 associated with first fluid source 16. On the other hand, whenever hydrostatic pressure in the secondary administration set 14 falls below the hydrostatic pressure of the primary administration set 12, fluid will flow through check valve 34 from the first fluid container 16 and into common tube 80. It should be appreciated that this will occur whenever the fluid level in secondary administration set 14 falls below the fluid level of primary administration set 12 or pinch clamp 88 is operated to pinch off or to occlude the pinchable section 58 to prevent fluid flow through the secondary administration set 14. If control valve 82 and pinchable section 58 are disconnected from controller 10, the system can work in this configuration without controller 10. The use of controller 10, however, greatly enhances the flexibility and accuracy of this system.

Use of controller 10 is accomplished by connecting pinchable section 58 and control valve 82 to controller 10 in the manner previously described. Also, first drop sensor 28 is operatively engaged with first drip chamber 30, and second drop sensor 54 is operatively engaged with second drip chamber 52. Using controller 10 the operator can select a drop rate for the flow of fluid through the primary administration set 12 by using preselect rate switch 96. Also, the operator preselects a desired drop rate for fluid flow through the secondary administration set 14 by using secondary rate switch 98. This selection process makes the information from rate switch 96 and rate switch 98 available to microprocessor 90 in the BCD and BCD compliment form for the purpose previously discussed.

The controller 10 begins actual operation when mode select switch 92 is turned to either the "primary only" position (not shown) or the "both" position (not shown). In either case upon activation of mode select switch 92, controller 10 automatically conducts several self-diagnostic tests. For example, microprocessor 90 is programmed to check for signals from primary drop sensor 28 and secondary drop sensor 54 to ensure that sensors 28 and 54 are respectively connected to primary administration set 12 and secondary administration set 14. Also, this check ensures that the primary administration set 12 and secondary administration set 14 are open for fluid flow and that obstructions such as clamp 62 have been removed. Microprocessor 90 also tests to ensure that latch 120 has been closed by sensing a signal from Hall effect device 116. Another diagnostic test performed by controller 10 is the activation of pinch motor 110. This is done to ensure operability of pinch motor 110 and to ensure that constrictor 114 is withdrawn from channel 118 to allow fluid flow pinchable section 58. Still another diagnostic test performed by controller 10 upon activation of power supply 94 by mode select switch 92 is the reciprocal cycling of the emergency motor 108 that is operatively associated with control valve 82. This test ensures the functionality and proper positioning of the drive shaft (not shown) which operatively connects emergency motor 108 with control valve 82. In addition to the above described diagnostic tests which are completed upon the initiation of operation of controller 10, microprocessor 90 of controller 10 is programmed to continuously monitor the operable status of controller 10 throughout its operation.

During operation microprocessor 90 senses the actual flow rate through the secondary system by signals from the drop sensor 54 which senses the drop rate in second drip chamber 52. Microprocessor 90 uses this information for comparison with the preselected drop rate established by the operator through manipulation of the rate switch 96. According to differences between the actual flow rate and the preselected desired rate, microprocessor 90, acting through PROM I/O 102, activates rotary motor 106 to adjust control valve 82 for the purpose of bringing the actual flow rate into compliance with the preselected rate for fluid flow through the secondary administration set 14. During the period of fluid flow through the second administration set 14, microprocessor 90 has continued to monitor drop sensor 28.

Upon completion of fluid flow through the secondary administration set 14, as sensed by drop sensor 54 on the cessation of drops in drip chamber 52, microprocessor 90 interacts with PROM I/O 100 to activate pinch motor 110. Pinch motor 110 then engages with pinching clamp 88 as described above. This action immediately stops fluid flow through the secondary administration set 14 and ensures reversal of hydrostatic pressure at check valve 34 to allow the commencement of fluid flow within the primary administration set 12.

As fluid flows from first fluid container 16 into primary administration set 12, drop sensor 28 signals microprocessor 90 with an indication of actual flow rate in primary administration set 12. This flow rate is then compared by microprocessor 90 with the preselected drop rate set by the operator using primary rate switch 96. Microprocessor 90 uses this information to activate PROM I/O 102 and operate rotary motor 106 to engage control valve 82 for controlling the flow of fluid through common tube 80.

It should be appreciated that the above described operation is affected when drip chamber 52 has adapted thereto a vent 50. In the case where a non-vented chamber (not shown) is used, it has been determined that there will be a period of time during which fluid can begin to flow through the primary administration set 12 despite the fact there is still fluid remaining to be delivered through the secondary administration set 14. Therefore, in the preferred embodiment microprocessor 90 is pre-programmed to operate the pinch clamp 88 in an either/ or mode. More specifically, microprocessor 90 is pre-programmed to operate pinch clamp 88 for engagement with the pinchable section 58 of secondary administration set 14 when either fluid flow ceases in the secondary administration set 14, as sensed by the drop sensor 54, or when sufficient fluid begins to flow in the primary administration set 12 as sensed by the drop sensor 28. In either of these situations, pinch clamp 88 will be operated to close or obstruct fluid flow through secondary administration set 14 to allow the commencement of fluid flow through the primary administration set 12.

While the particular piggyback IV administration system as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. An apparatus for the administration of intravenous fluids to a patient comprising:
   a first fluid container;
   a primary administration set in fluid communication with said first fluid container;
   a second fluid container;
   a second administration set having a pinchable section and connected in fluid communication with said second fluid container;
   a common tube for transferring fluid to the patient;
   means for connecting said primary and said secondary administration sets in fluid communication with said common tube;
   means for sequencing fluid flow through said secondary and said primary administration sets, said sequencing means comprising a check valve in the fluid lines of said primary administration set to prevent fluid flow in said primary administration set when the hydrostatic pressure in said secondary set exceeds the hydrostatic pressure in said primary set;
   means for sensing actual flow rates through said secondary and said primary administration sets;
   a controller having means operatively associated with said pinchable section to selectively prevent fluid flow through said secondary administration set, said controller further comprising means to preselect flow rates for said primary and secondary adminsitration sets, said controller operatively associated with said sensing means in said primary and secondary administration sets and having means for operatively engaging with said common tube to maintain the sensed actual flow rate at the respective preselected flow rate.

2. An apparatus for the administration of intravenous fluids to a patient as recited in claim 1 wherein said engaging means between said controller and said common tube comprises a control valve disposed in the fluid line of said common tube and operatively connected to said controller for maintaining fluid flow through said common tube at the respective preselected flow rate.

3. An apparatus for the administration of intravenous fluid to a patient comprising:
   a first fluid container;
   a primary administration set attached to said first fluid container comprising, in sequence downstream from said first fluid container, a first drip chamber, a check valve and a connector;
   a second fluid container;
   a secondary administration set attached to said second fluid container comprising, in sequence downstream from said second fluid container, a second drip chamber, a pinchable section and a linking means engagable with said connector;
   a common tube for directing fluid flow from said connector to the patient and having a flow control valve operatively associated therewith for controlling fluid flow therethrough;
   means for elevating the hydrostatic pressure in said secondary administration set above the hydrostatic pressure in said primary administration set to prevent fluid flow through said one-way valve when fluid is in said second fluid container and is flowing through said secondary set;
   a first drop sensor operatively associated with said first drip chamber for detecting the actual flow rate therethrough;
   a second drop sensor operatively associated with said second drip chamber for detecting the actual flow rate therethrough; and
   a controller operatively connecting said first drop sensor and said second drop sensor with said control valve for adjusting the actual flow rate through said respective drip chamber to correspond to a preselected valve, said controller further comprising pinching means operatively associated with said pinchable section to prevent flow in said secondary set after flow in said second drip chamber ceases.

4. An apparatus for the administration of intravenous fluid to a patient comprising:
   a primary administration set sequentially comprising a first drip chamber, a check valve and a connector;
   a first fluid container in fluid communication with said first drip chamber;
   a secondary administration set sequentially comprising a second drip chamber, a pinchable section and a linking means connectable in fluid communication with said connector;
   a second fluid container in fluid communication with said second drip chamber;
   means to raise hydrostatic pressure in said secondary administration set above the hydrostatic pressure in said primary administration set;
   a common tube in fluid communication with said connector, for transferring fluid to a patient;
   a control valve operatively associated with said common tube;
   a controller having means operatively associated with said pinchable section to selectively prevent fluid flow through said secondary administration set, said controller further comprising means to select independent fluid flow rates for the respective administration sets;
   a first sensor means connected to said controller and associated with said primary administration set for sensing fluid flow therethrough;
   a second sensor means connected to said controller and associated with said secondary administration set for sensing fluid flow therethrough; and
   means for connecting said control valve to said controller to operate said control valve for adjusting fluid flow therethrough to maintain sensed flow rates at the respective selected flow rate.

5. An apparatus for the administration of intravenous fluids to a patient comprising:
   a control valve;
   a first fluid container;
   a second fluid container;
   a primary administration set connecting said first fluid container in fluid communication with said control valve;
   a second administration set having a pinchable section and connecting said second fluid container in fluid communication with said control valve;
   means for sequencing fluid flow through said secondary set and said primary set;
   a first sensor means and a second sensor means respectively associated with said primary and said secondary administration sets for sensing fluid flow rates therethrough;
   a controller operatively connected with said first and second sensor means and having means for selecting desired flow rates for said respective administration sets, and said controller further comprising means operatively associated with said pinchable section to selectively prevent fluid flow through said secondary administration set;
   means operatively connecting said controller with said control valve to (1) compare the sensed flow rate with the selected flow rate and (2) accordingly adjust said control valve to maintain fluid flow therethrough at the selected flow rate; and
   means for transferring fluid from said control valve to said patient.

6. An apparatus for the administration of intravenous fluids to a patient as recited in claim 5 wherein said sequencing means comprises a check valve in the fluid line of said primary administration set to prevent fluid flow in said primary administration set when the hydrostatic pressure in said secondary set exceeds the hydrostatic pressure in said primary set.

* * * * *